United States Patent [19]

Moellmann et al.

[11] Patent Number: 5,630,802
[45] Date of Patent: May 20, 1997

[54] DEVICE FOR INTRODUCING A CATHETER INTO A BODY CAVITY

[75] Inventors: Michael Moellmann, Muenster; Kevin P. Woehr, Felsberg, both of Germany

[73] Assignee: B. Braun Melsungen AG, Melsungen, Germany

[21] Appl. No.: 425,865

[22] Filed: Apr. 20, 1995

[30] Foreign Application Priority Data

Apr. 25, 1994 [DE] Germany .......................... 44 14 345.1
Dec. 8, 1994 [DE] Germany .......................... 44 43 672.6

[51] Int. Cl.⁶ .......................................... A61M 25/00
[52] U.S. Cl. .................................... 604/164; 604/158
[58] Field of Search .................................. 604/158, 159, 604/160, 161, 164, 51

[56] References Cited

U.S. PATENT DOCUMENTS 5,232,442  8/1993  Johnson et al. .
5,306,239  4/1994  Gurmarnik et al. ............... 604/158 X
5,380,292  1/1995  Wilson ................................. 604/158 X
5,470,318  11/1995  Griffith, III et al. ............... 604/158 X

*Primary Examiner*—Sam Rimell
*Attorney, Agent, or Firm*—Loeb & Loeb LLP

[57] ABSTRACT

A catheter for spinal anesthesia has a needle arranged therein. The length of the needle is smaller than the length of the catheter. The rear end of the needle is connected to a handling thread for pulling the needle out of the catheter towards the proximal end. The needle is designed as a hollow needle with a lateral opening. When advancing the tip of the needle into the subarachnoid space, liquor flows through the opening into the catheter, allowing for verification of successful puncture. During puncture of the dura with the tip of the needle, the puncture hole is widened by the front end of the catheter so that the catheter fills the puncture hole completely. After puncture, the needle is withdrawn by pulling the handling thread.

11 Claims, 2 Drawing Sheets

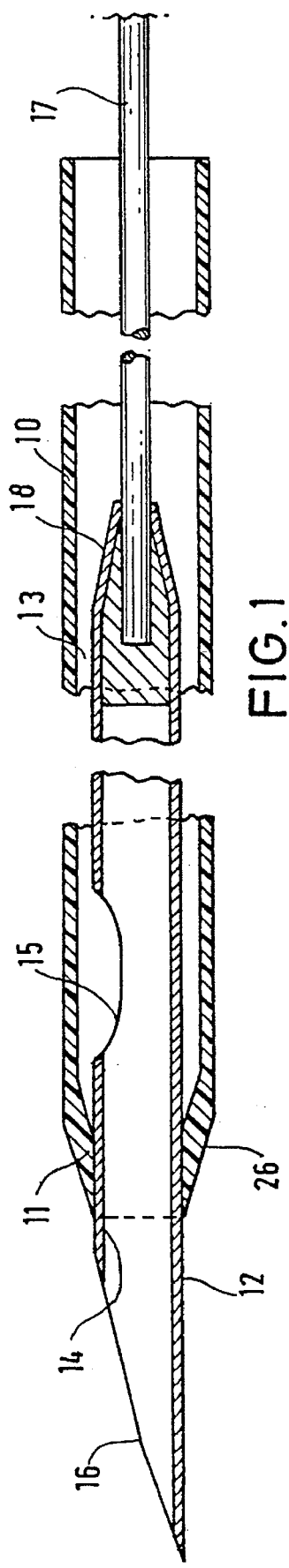
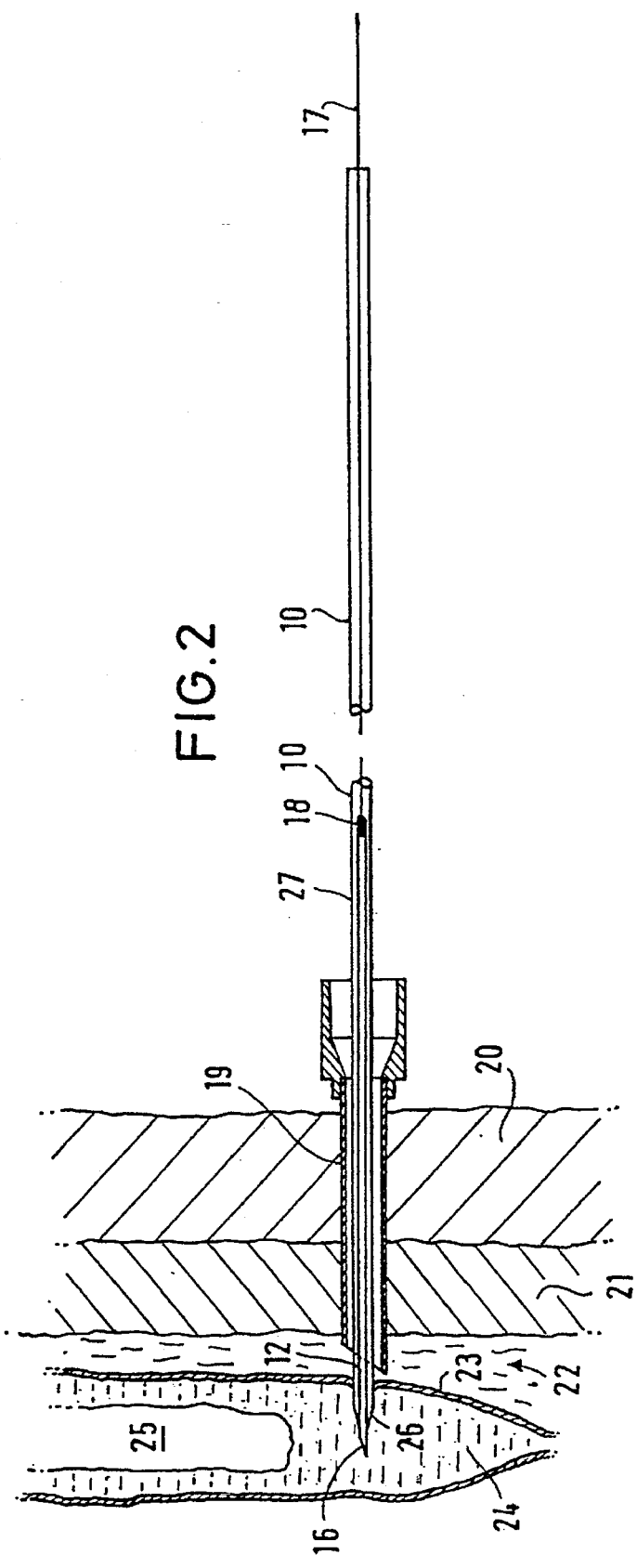

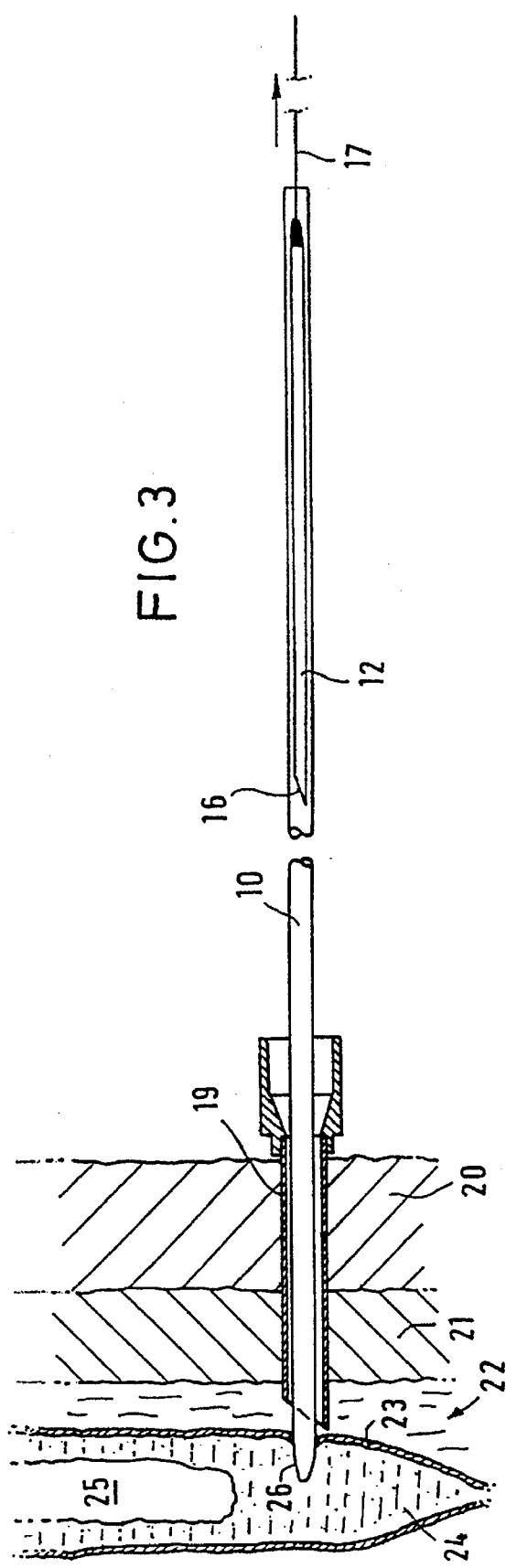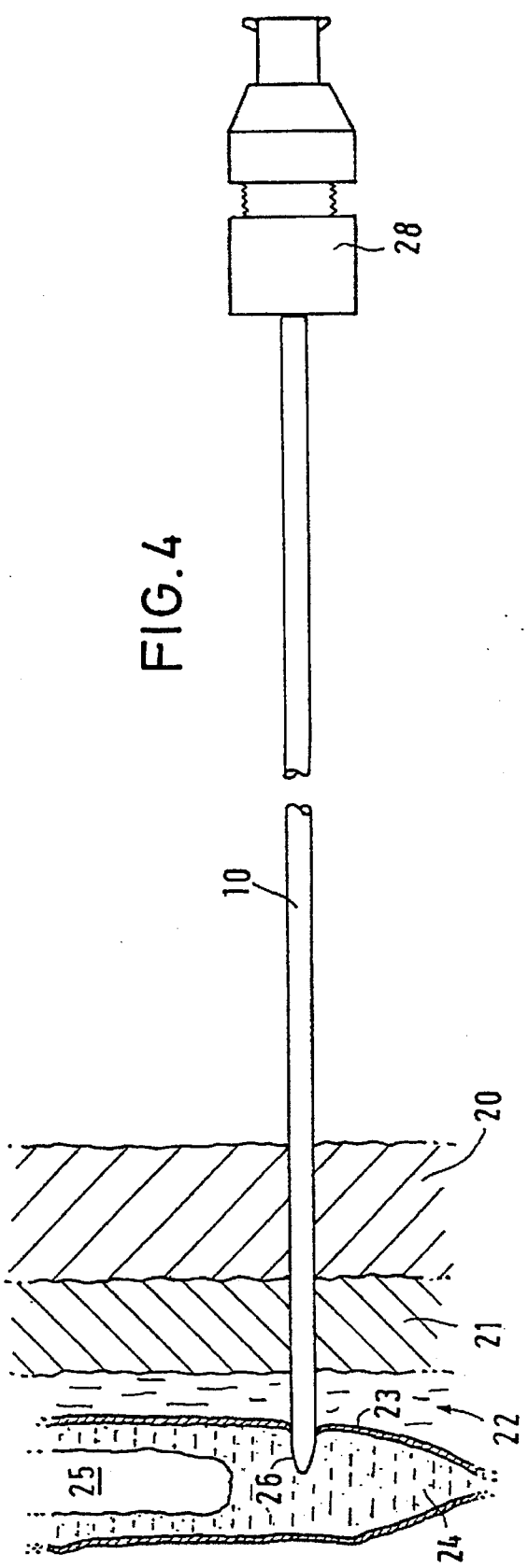

DEVICE FOR INTRODUCING A CATHETER INTO A BODY CAVITY

BACKGROUND OF THE INVENTION

The invention relates to a device for introducing a catheter into a body cavity, particularly for introducing an in-dwelling catheter into the subarachnoid space to perform continuous spinal anesthesia.

In continuous spinal anesthesia (CSA), when a catheter is introduced into the subarachnoid space (spinal space), the dura delimiting this space is pierced. These dura punctures frequently result in postspinal pain (post dura puncture headache (PDPH)). Such postspinal headaches are caused by an outflow of liquor cerebrospinalis from the subarachnoid space after removal of the puncture needle and introduction of the catheter which has a smaller diameter than the puncture hole generated in the dura.

A known device for introducing a catheter into the subarachnoid space according to U.S. Pat. No. 5,232,442 comprises a catheter having an elongated needle arranged therein. The needle extends along the complete length of the catheter and protrudes out of both ends of the catheter. The (distal) patient end of the needle is provided with a non-cutting tip. First, an insertion cannula is advanced into the epidural space. Subsequently, an auxiliary tube is moved through the insertion cannula and is set against the dural wall without cutting into it. The catheter accommodating the needle is advanced through the auxiliary tube. The tip of the needle pierces the dural wall and together with the catheter generates a hole corresponding to the outer diameter of the catheter. In this manner, the catheter is advanced into the subarachnoid space without undesired escape of liquor. Then, the needle is withdrawn from the catheter, and the catheter can be connected to a syringe for administering an anesthetic. In the above known device, the needle which—is flexible but must have relatively large stiffness—extends along the complete length of the catheter. Thus, the catheter together with the needle accommodated therein has a considerable stiffness, which impairs the handling of the catheter.

It is an object of the invention to provide a device for introducing a catheter which allows for easier handling of the catheter.

SUMMARY OF THE INVENTION

The insertion device according to the invention is provided with a needle having a shorter length than the catheter so that the needle will reduce the flexibility of the catheter only along a short part of the length of the catheter. The needle is connected to a flexible, easily bendable handling thread of a small diameter for pulling the needle out of the catheter from the patient-side end after the catheter has been set. While the catheter is being set, the needle protrudes from the rear end. On this end, the catheter tightly surrounds the needle, i.e. without leaving a gap. By advancing the catheter along with the needle, an inner wall of the body—e.g., the dura—can be punctured, with the needle tip generating the puncture hole and the catheter then widening this hole. When the needle is subsequently withdrawn from the catheter, the catheter fills the hole in the body wall completely so that no body liquid can flow past the catheter and out of the cavity delimited by the body wall.

The device of the invention is particularly suited for setting an in-dwelling catheter into the spinal space when a local anesthetic is to be injected. Further, the device is useful for injecting anesthetics into other parts of the body, or for drainage purposes.

According to a preferred embodiment of the invention, the lumen of the catheter on the patient-side end is formed with a constricted portion tightly enclosing a part of the needle, an annular gap being arranged between the needle and the catheter behind the constricted portion. In this configuration, only the patient-side end of the catheter has a sealing effect against the needle, with an annular gap being provided behind the constricted portion. Preferably, the patient-side portion of the needle is formed as a blind bore having a lateral opening formed therein. Thus, liquor can enter the catheter from the punctured body cavity through the blind bore and the lateral opening. The liquor flowing into the catheter visually indicates that the puncture has been successful and the correct body cavity has been hit. In this manner, for instance, it can be detected whether a blood vessel has been possibly punctured by mistake. Should a blood vessel have been punctured, blood would flow into the translucent catheter and this condition would be noticed by the user.

Generally, the device of the present invention can be used for catheters of a wide range of sizes, the needle being adapted to the respective lumen of the catheter. If the device for introducing a catheter is used for spinal anesthesia, the catheter can be formed as a microcatheter having an outer diameter below G26 size. However, for this purpose, it is recommended to use a larger-diametered catheter with a size ranging from G20 to G24 to avoid locally nerve-toxic concentration of the local anesthetic (cauda equina syndrome).

BRIEF DESCRIPTION OF THE DRAWINGS

An embodiment of the invention will be explained in greater detail hereunder with reference to the drawings.

FIG. 1 is a longitudinal sectional view of parts of the catheter insertion device, FIG. 2 is a view illustrating the puncture of the dura by the needle tip protruding from the catheter, FIG. 3 is a view illustrating the withdrawal of the needle from the catheter after puncture has been terminated, and FIG. 4 is a view of the set catheter having an adapter connected to its rear end.

DESCRIPTION OF THE PREFERRED EMBODIMENT

According to FIG. 1, the device of the present invention comprises a catheter 10 formed as an elongated hose. The size of the catheter lies in the range from G20 to G24. Catheter 10 has a catheter lumen of a uniform constant width, except for a constricted portion 11 at the patient-side end of catheter 10 where the catheter lumen or diameter is reduced.

Catheter 10 has a needle 12 inserted therein. The diameter of needle 12 is smaller than the lumen of catheter 10, leaving an annular space 13 between the wall of catheter 10 and needle 12. On the patient-side end, however, the wall of catheter 10 has its constricted portion 11 enclosing the needle 12 in a tight and sealing manner. The axial length of constricted portion 11 is about half the size of the catheter diameter.

Needle 12 is designed as a hollow needle, i.e. is formed with a longitudinal blind bore 14 being open towards the distal end of needle 12. Needle 12 has at least one lateral opening 15 providing a lateral outlet for liquid flowing into blind bore 14. Opening 15 is arranged behind the constricted portion 11 of catheter 10.

The tip 16 of needle 12, protruding from catheter 10, is provided with a ground bevel. This bevel is non-coring, i.e. is designed to punch no cores, i.e., when advancing the tip 16, no tissue nuclei are punched out from the tissue and, therefore, blocking of the blind bore 14 is avoided. On the other hand, tip 16 is sharp enough for cutting, i.e. it is adapted to cut through tissue and fibers.

The diameter of needle 12 is substantially constant along the complete length of the needle. Needle 12 covers a length of several centimeters within catheter 10. A flexible handling thread 17 is attached to the rear (proximal) end of needle 12, the diameter of handling thread 17 being smaller than that of needle 12 and not larger than the inner diameter of needle 12. The rear end of needle 12 is provided with a truncated bevelled portion 18 providing a smooth transition from the needle diameter to the smaller diameter of handling thread 17. Handling thread 17 serves for pulling needle 12 out of catheter 10.

FIGS. 2–4 illustrate the process of setting of the catheter in the subarachnoid space. First, an insertion cannula 19, containing a mandrel (not shown) is advanced through the skin 20 and the ligamentum flavum 21 into the epidural space 22. Then, the mandrel is withdrawn from the insertion cannula 19 so that the catheter 10 having the needle 12 arranged therein can be inserted into the insertion cannula 19. The tip of insertion cannula 19 will then be in a position before the dura 23 enclosing the subarachnoid space (spinal space) 24. The subarachnoid space 24 contains the cauda equina 25, and the rest of this space is filled with liquor.

In the relative position shown in FIG. 1, catheter 10 and needle 12 are pierced through dura 23, while the catheter tip 16 generates the puncture hole which is subsequently widened by a bevelled portion 26 at the front end of the catheter 10.

To advance the needle 12, catheter 10 is squeezed in the region 27 outside insertion cannula 19 by the user's thumb, index finger and middle finger. The rear end of needle 12 is located in this catheter region 27 so that the user can grip the needle 12 through the catheter wall so as to advance the needle along with the catheter. For this reason, needle 12 is longer than insertion cannula 19 but considerably shorter than catheter 10.

The backflow of the liquor is observed outside insertion cannula 19 to verify that the dura 23 has been pierced. If required, a Tuohy Borst adapter 28 (FIG. 4) is mounted on the catheter end accommodating the handling thread 17, allowing the use of a syringe to quicken the backflow by aspiration. For this reason, the handling thread 17 at the rear end must not have any thickened portion or any gripping piece because, otherwise, it would be impossible to connect the Tuohy Borst adapter while needle 12 and handling thread 17 are in their position within catheter 10.

FIG. 3 illustrates the withdrawal of needle 12 by pulling the handling thread 17 towards the rear end. In doing so, the user can hold catheter 10 in place with the other hand so that the catheter will not move along with the needle. After withdrawal of needle 12, also insertion cannula 19 is removed by pulling it back over catheter 10.

FIG. 4 is a view of the set catheter 10 which is completely enclosed by the dura 23 so that no liquor can bypass the catheter 10 and escape from the subarachnoid space 24. The rear end of catheter 10 carries a Tuohy Borst adapter 28 mounted thereon and suited for connection of a syringe. A syringe can be used for injecting an anesthetic through catheter 10 into subarachnoid space 24.

We claim:

1. A device for introducing a catheter into a body cavity, comprising a catheter having a proximal end and a distal end, and a needle having a tip and being arranged to be moved within the catheter and to be positioned in such a manner that the tip of the needle protrudes from the catheter on the distal end thereof, wherein the needle is shorter than the catheter and has a closed proximal end attached to a flexible handling thread having a diameter smaller than that of the needle and protruding from the proximal end of the catheter in each position of the needle within the catheter.

2. The device according to claim 1, wherein the lumen of the catheter has a first portion formed therein at the distal end of the catheter, the first portion tightly enclosing a part of the length of the needle, and an annular gap is provided between the needle and the catheter adjacent the proximal end of the first portion.

3. The device according to claim 1, wherein the distal portion of the needle is formed as a blind bore, the blind bore being provided with a lateral opening.

4. The device according to claim 1, wherein the tip of the needle is a cutting tip.

5. The device according to claim 1, wherein the tip of the needle is provided with a non-coring bevel.

6. The device according to claim 1, wherein the distal end of the catheter has a truncated outer surface.

7. A device for introducing a catheter into a body cavity, comprising a catheter having a proximal end and a distal end, and a needle having a tip and being arranged to be moved within the catheter and to be positioned in such a manner that the tip of the needle protrudes from the catheter on the distal end thereof, wherein the needle is shorter than the catheter and is attached to a handling thread having a diameter smaller than that of the needle and protruding from the proximal end of the catheter in each position of the needle within the catheter, wherein the proximal end of the needle is truncated.

8. The device according to claim 1, wherein an adapter, to be mounted on the catheter, is provided for connection of a syringe to the catheter.

9. The device according to claim 1, wherein an insertion cannula is provided for advancing the catheter together with the needle arranged therein, the length of the needle being larger than that of the insertion cannula.

10. The device according to claim 1, wherein the size of the catheter is in the range from G20 to G24.

11. The device according to claim 1, wherein the handling thread has a uniform width without any thickened portion or any gripping piece.

* * * * *